United States Patent [19]

Berg

[11] Patent Number: 5,460,700
[45] Date of Patent: Oct. 24, 1995

[54] SEPARATION OF 1-HEXENE FROM HEXANE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 246,245

[22] Filed: May 19, 1994

[51] Int. Cl.$^6$ .................. B01D 3/40; C07C 7/08
[52] U.S. Cl. ................. 203/60; 203/62; 203/63; 585/864; 585/866
[58] Field of Search .................. 203/60, 63, 62, 203/56; 585/866, 864

[56] References Cited

U.S. PATENT DOCUMENTS

| | | | |
|---|---|---|---|
| 5,085,740 | 2/1992 | Lee et al. | 203/56 |
| 5,100,515 | 3/1992 | Lee et al. | 203/64 |
| 5,106,460 | 4/1992 | Berg | 203/63 |
| 5,256,259 | 10/1993 | Berg et al. | 203/62 |

Primary Examiner—Wilbur Bascomb, Jr.

[57] ABSTRACT

1-Hexene is difficult to separate from hexane by conventional distillation or rectification because of the proximity of their boiling points. 1-Hexene can be readily separated from hexane by extractive distillation. Effective agents are hexyl acetate, methyl amyl alcohol and acetophenone.

1 Claim, No Drawings

SEPARATION OF 1-HEXENE FROM HEXANE BY EXTRACTIVE DISTILLATION

FIELD OF THE INVENTION

This invention relates to a method for separating 1-hexene from hexane using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

There are a number of commercial processes which produce mixtures of hydrocarbons that boil very close together, e.g. petroleum refining and Fischer-Tropsch. Two close boiling compounds frequently produced are 1-hexene, b.p.=64° C. and hexane, b.p. =69° C. The relative volatility between these two is 1.07 which makes it virtually impossible to separate them by conventional rectification. Extractive distillation would be an attractive method of effecting the separation of 1-hexene from hexane if agents can be found that (1) will create a large apparent relative volatility between 1-hexene and hexane and (2) are easy to recover from hexane. Table 1 shows the relative volatility required to obtain 99% purity. With no agent, the relative volatility is 1.07 and 181 actual plates are required. With an agent giving a relative volatility of 1.35, only 41 actual plates are required.

OBJECTIVE OF THE INVENTION

The object of this invention is to provide a process or method of extractive distillation that will enhance the relative volatility of 1-hexene from hexane in their separation in a rectification column. It is a further object of this invention to identify organic compounds which in addition the above constraints, are stable, can be separated from hexane and recycled to the extractive distillation column with little decomposition.

TABLE 1

Theoretical and Actual Plates Required vs. Relative Volatility for 1-Hexene - Hexane Separation

| Relative Volatility | Theoretical Plates Required At Total Reflux, 99% Purity | Actual Plates Required 75% Efficiency |
| --- | --- | --- |
| 1.07 | 136 | 181 |
| 1.20 | 50 | 67 |
| 1.30 | 35 | 47 |
| 1.35 | 31 | 41 |

SUMMARY OF THE INVENTION

The objects of this invention are provided by a process for the separation of 1-hexene from hexane which entails the use of certain organic compounds when employed as the agent in extractive distillation.

DETAILED DESCRIPTION OF THE INVENTION

I have discovered that certain organic compounds will greatly improve the relative volatility of 1-hexene to hexane and permit the separation of 1-hexene from hexane by rectification when employed as the agent in extractive distillation. Table 2 lists the compounds that I have found to be effective. They are isobutanol, isoamyl alcohol, 1-hexanol, amyl acetate, methyl amyl alcohol, hexyl acetate, butyl formate, isoamyl formate, ethyl butyrate, methyl butyrate, 3-methyl-3-pentanol, isobutyl isobutyrate, butyl butyrate, hexyl formate, isopropyl butyrate, pinacolone, 2-octanone, 2,6-dimethyl-4-heptanone, propiophenone and acetophenone.

THE USEFULNESS OF THE INVENTION

The usefulness or utility of this invention can be demonstrated by referring to the data presented in Tables 1 and 2. All of the successful agents show that 1-hexene can be separated from hexane by means of extractive distillation in a rectification column and that the ease of separation as measured by relative volatility is considerable.

TABLE 2

Effective Extractive Distillation Agents For Separating 1-Hexene From Hexane

| Compounds | Relative Volatility |
| --- | --- |
| None | 1.07 |
| Isobutanol | 1.18 |
| Isoamyl alcohol | 1.23 |
| 1-Hexanol | 1.20 |
| Amyl acetate | 1.25 |
| Methyl amyl alcohol | 1.25 |
| Hexyl acetate | 1.27 |
| Butyl formate | 1.20 |
| Isoamyl formate | 1.20 |
| Ethyl butyrate | 1.20 |
| 3-Methyl-3-pentanol | 1.20 |
| Methyl butyrate | 1.20 |
| Isobutyl isobutyrate | 1.20 |
| Butyl butyrate | 1.20 |
| Hexyl formate | 1.35 |
| Isopropyl butyrate | 1.20 |
| Pinacolone | 1.20 |
| 2-Octanone | 1.20 |
| 2,6-Dimethyl-4-heptanone | 1.25 |
| Propiophenone | 1.30 |

TABLE 2-continued

Effective Extractive Distillation Agents For
Separating 1-Hexene From Hexane

| Compounds | Relative Volatility |
|---|---|
| Acetophenone | 1.23 |

WORKING EXAMPLES

Example 1: Eighty grams of hexane, 20 grams of 1-hexene and 50 grams of hexyl acetate were charged to a vapor-liquid equilibrium still and refluxed for six hours. Analysis indicated a vapor composition of 29.3% 1-hexene, 70.7% hexane; a liquid composition of 24.6% 1-hexene, 75.4% hexane. This is a relative volatility of 1.27.

Example 2: A solution comprising 100 grams 1-hexene and 50 grams of hexane was placed in the stillpot of a 5.5 theoretical plate glass perforated plate rectification column. When refluxing began, an extractive agent comprising acetophenone was pumped into the top of the column at a rate of 15 ml/min. The temperature of the extractive agent as it entered the column was 134° C. After establishing the feed rate of the extractive agent, the heat input to the 1-hexene—hexane in the stillpot was adjusted to give a total reflux rate of 40 ml/min. After two hours of operation, overhead and bottoms samples were collected and analysed by gas chromatography. The overhead composition was 75.3% 1-hexene, 24.7% hexane and the bottoms composition was 48.5% 1-hexene, 51.5% hexane. This gives a relative volatility of 1.23 for each theoretical plate.

I claim:

1. A method for recovering 1-hexene from a mixture of 1-hexene and hexane which comprises distilling a mixture of 1-hexene and hexane in the presence of from one to five parts by weight of an extractive agent per part of 1-hexene - hexane mixture, recovering the 1-hexene as overhead product and obtaining the hexane and the extractive agent as bottoms product, wherein said extractive agent consists of one material selected from the group consisting of isobutanol, isoamyl alcohol, amyl acetate, hexyl acetate, butyl formate, isoamyl formate, ethyl butyrate, methyl butyrate, isobutyl isobutyrate, butyl butyrate, hexyl formate, isopropyl butyrate, pinacolone, 2-octanone, 2,6-dimethyl-4-heptanone, propiophenone and acetophenone.

* * * * *